United States Patent
Weber-Hovendahl et al.

(10) Patent No.: US 10,239,061 B2
(45) Date of Patent: Mar. 26, 2019

(54) TURN-SECURE RACK

(71) Applicant: Brooks Automation, Inc., Chelmsford, MA (US)

(72) Inventors: Lars Weber-Hovendahl, Hvalsø (DK); Michael Gabs Kaagaard Nielsen, Lejre (DK)

(73) Assignee: Brooks Automation, Inc., Chelmsford, MA (US)

( * ) Notice: Subject to any disclaimer, the term of this patent is extended or adjusted under 35 U.S.C. 154(b) by 0 days.

(21) Appl. No.: 15/549,127

(22) PCT Filed: Feb. 5, 2016

(86) PCT No.: PCT/EP2016/052470
§ 371 (c)(1),
(2) Date: Aug. 4, 2017

(87) PCT Pub. No.: WO2016/124729
PCT Pub. Date: Aug. 11, 2016

(65) Prior Publication Data
US 2018/0021784 A1    Jan. 25, 2018

(30) Foreign Application Priority Data
Feb. 6, 2015 (DK) .................................. 2015 00065

(51) Int. Cl.
*B01L 9/06* (2006.01)
*G01N 35/02* (2006.01)
*G01N 35/04* (2006.01)

(52) U.S. Cl.
CPC ........... *B01L 9/06* (2013.01); *B01L 2200/087* (2013.01); *B01L 2200/12* (2013.01);
(Continued)

(58) Field of Classification Search
CPC ................. B01L 9/06; B01L 2300/041; B01L 2300/0851; B01L 2300/123;
(Continued)

(56) References Cited

U.S. PATENT DOCUMENTS 1,188,146 A * 6/1916 Bogley .................. A47B 73/00
                                                            211/126.1
3,379,315 A * 4/1968 Broadwin ............. B01L 3/0217
                                                            211/189
(Continued)

FOREIGN PATENT DOCUMENTS

EP            1882949 A1     1/2008
WO    WO 2010/056884 A1     5/2010
(Continued)

OTHER PUBLICATIONS

ANSI/SLAS 1-2004 (formerly recognized as ANSI/SBS 1-2004) ANSI American National Standards Institute, SLAS Society for Laboratory Automation and Screening, for Microplates—Footprint Dimensions, Oct. 12, 2011, 8 pages.
(Continued)

*Primary Examiner* — Jennifer E. Novosad
(74) *Attorney, Agent, or Firm* — Hamilton, Brook, Smith & Reynolds, P.C.

(57) ABSTRACT

A SBS-standard test tube rack is provided which is suitable for use in automated capping and de-capping of flat bottomed test tubes, in particular flat bottomed glass vials, both for individual test tube capping and de-capping as well as simultaneous capping and de-capping of all test tubes in the aforementioned SBS-standard test tube rack. The rack comprises a top tier having a plurality of apertures and a bottom tier that comprises a friction tier of high friction material. The bottom of each well in the rack is formed of the high friction material.

8 Claims, 4 Drawing Sheets

(52) U.S. Cl.
CPC . *B01L 2300/041* (2013.01); *B01L 2300/0851* (2013.01); *B01L 2300/123* (2013.01); *G01N 35/028* (2013.01); *G01N 2035/0405* (2013.01); *G01N 2035/0418* (2013.01); *G01N 2035/0429* (2013.01)

(58) Field of Classification Search
CPC ........... B01L 2200/087; B01L 2200/12; G01N 35/028; G01N 2035/0405; G01N 2035/0418; G01N 2035/0429; A47B 73/00; A47B 81/007; A47F 7/28; A47F 7/283; A47G 23/02
USPC .................. 211/74, 85.18, 60.1; 206/446
See application file for complete search history.

(56) References Cited

U.S. PATENT DOCUMENTS

| | | | | |
|---|---|---|---|---|
| 3,643,812 | A * | 2/1972 | Mander | B01L 9/06 206/443 |
| 4,073,623 | A * | 2/1978 | Bodart | B01L 9/06 23/259 |
| 4,124,122 | A * | 11/1978 | Emmitt | B01L 9/06 211/74 |
| RE30,276 | E * | 5/1980 | Rohde | B01L 3/50825 211/74 |
| 4,284,603 | A * | 8/1981 | Korom | B01L 9/06 210/323.1 |
| 4,389,374 | A * | 6/1983 | Sutton | B04B 5/0421 206/201 |
| 4,407,958 | A * | 10/1983 | DeGraff, Jr. | B01L 9/06 211/194 |
| 4,588,095 | A * | 5/1986 | Mehra | B01L 9/06 211/126.1 |
| 5,127,895 | A * | 7/1992 | Pawlovich | B04B 5/0414 215/277 |
| 5,133,939 | A * | 7/1992 | Mahe | B01L 9/06 422/104 |
| 5,148,919 | A * | 9/1992 | Rubin | B01L 9/06 206/443 |
| 5,632,388 | A * | 5/1997 | Morrison | B01L 9/06 211/170 |
| 5,950,832 | A * | 9/1999 | Perlman | B01L 9/06 206/446 |
| 5,996,818 | A * | 12/1999 | Boje | B01L 9/06 206/443 |
| D506,833 | S * | 6/2005 | Wescott, III | B01L 9/06 422/411 |
| 9,144,801 | B2 * | 9/2015 | Johnson | B01L 9/06 |
| 2002/0108917 | A1 * | 8/2002 | Maruyama | B01L 9/06 211/74 |
| 2006/0210432 | A1 | 9/2006 | Victor | |
| 2009/0028754 | A1 | 1/2009 | Robb | |
| 2013/0318915 | A1 * | 12/2013 | Iskarous | G01N 35/04 53/264 |
| 2014/0008249 | A1 | 1/2014 | Mueller | |
| 2015/0175398 | A1 | 6/2015 | Christensen et al. | |
| 2016/0178550 | A1 * | 6/2016 | Hegel | G01N 35/04 324/691 |
| 2017/0152130 | A1 * | 6/2017 | Kakuda | B65D 39/04 |
| 2018/0021784 | A1 * | 1/2018 | Weber-Hovendahl | B01L 9/06 |

FOREIGN PATENT DOCUMENTS

| | | |
|---|---|---|
| WO | WO 2014/023683 A2 | 2/2014 |
| WO | WO 2014/023683 A3 | 2/2014 |

OTHER PUBLICATIONS

Biosero Engineering Solutions for Science, VIALCAP24 Capper/DeCapper Product Data Sheet—Preliminary Specifications, 2014, 1 page.
International Search Report and Written Opinion of the International Searching Authority for International Application No. PCT/EP2016/052470; entitled "Turn-Secure Rack", dated Mar. 5, 2016, 11 pages.
International Preliminary Report on Patentability, PCT/EP2016/052470, entitled, "Turn-Secure Rack", dated Aug. 8, 2017.

* cited by examiner

TURN-SECURE RACK

RELATED APPLICATIONS

This application is the U.S. National Stage of International Application No. PCT/EP2016/052470, filed Feb. 5, 2016, which designates the U.S., published in English, and claims priority under 35 U.S.C. §§ 119 or 365(c) to Denmark Application No. PA201500065, filed Feb. 6, 2015. The entire teachings of the above applications are incorporated herein by reference.

FIELD

In the field of automatic capping and de-capping of smooth test vials there is proposed a turn-secure rack suitable for use with standard automatic capping and de-capping devices.

BACKGROUND

High value biological samples are often stored and processed using so-called SBS format racks containing a plurality of test tubes. SBS format racks confer to ANSI/SLAS 1-2004 standards and have a standardized footprint of 127.76 mm±0.25 mm×85.48 mm±0.25 mm but varying number of test tube apertures. Such racks may contain, for example, 96 test tubes in an array of 8 by 12 apertures or wells designed to hold the tubes securely. The test tubes and their contents may be maneuvered in a processing system, for example between a cold store and various processing stations and may be required to be filled (partly or fully) or processed simultaneously or individually.

Conventionally, capping and de-capping of test tubes has either been carried out by hand or else by means of a capping and de-capping unit one test tube at a time, either while the test tubes are still held in the rack or after they have been separated from the rack. This is not only tedious (particularly in the case of manual capping and de-capping), but also slow as it is usual for multiple tubes to require processing in the same way at the same time.

Solutions (e.g. EP 1882949 or WO 2014023683) are known for capping and de-capping test tubes in standard laboratory test tube racks, such as e.g. the aforementioned SBS format test tube racks.

Automated capping and de-capping of screw cap test tubes involves mechanisms to create a rotational and opposite relative movement of screw cap and test tube. To this purpose both the screw cap and the test tube must be kept from slipping and co-rotating during the capping and de-capping operations. Most automated capping and de-capping devices exert a slight pressure on the screw cap and test tube assemblies during the capping and de-capping operations, thereby increasing the friction force of test tube to test tube rack. However, for many uses and test tubes this slight pressure is not sufficient to keep a test tube from co-rotating with its screw cap. This problem so far has limited the uses of automated capping and de-capping unnecessarily.

WO 2014023683, which is hereby incorporated by reference, discloses a capping and de-capping apparatus 100 (FIG. 4) for capping and de-capping capable tubes 112 disposed in a rack 111 with a two dimensional array of apertures for holding said tubes, the apparatus comprising a rack support 110 for supporting the rack; a head unit 120 supporting a two-dimensional array 121 of capping and de-capping grippers 122, each capping and de-capping gripper including a capping and de-capping socket unit 123 configured for engaging and retaining a cap 113, the capping and de-capping grippers 122 being aligned with tube apertures defined by the array in the rack; a drive mechanism 130 for moving the rack support 110 and head unit 120 relatively towards and away from one another, to cause engagement or disengagement of at least one capping and de-capping socket unit 123 with or from a cap 113 of at least one tube 112; and a drive system for rotating at least one capping and de-capping gripper 122 and the capping and de-capping socket unit 123 attached thereto, wherein rotation of the capping and de-capping socket unit, after engagement of the at least one capping and de-capping socket unit with at least one cap 113, causes attachment of the at least one cap to the at least one tube 112 within the rack 111 when the at least one capping and de-capping gripper 122 rotates in one direction and causes detachment of the at least one cap from the at least one tube when the at least one capping and de-capping gripper rotates in the opposite direction, characterized in that the at least one capping and de-capping gripper 122 has a throughgoing passage extending through the at least one capping and de-capping gripper and the capping and de-capping socket unit 123 attached thereto, an ejector pin moveably arranged within the through going passage; and wherein the ejector pin is configured to perform a translational movement relative to the at least one capping and de-capping gripper 122 and capping and de-capping socket unit 123 attached to the gripper thereby effecting a release of a cap retained within the capping and de-capping socket unit. The apparatus 100 further includes a drive system 150 and a control unit 160. The capping and de-capping apparatus of WO 2014023683 is particularly suitable for both individual and simultaneous capping and de-capping of test tubes of tubes which are rotationally restrained by the rack during the automated capping and de-capping operations.

In order for the test tubes to be easily inserted and retracted from a standard rack, the apertures or wells are often designed with a slight clearance or positive tolerance, such that the test tubes do not encounter any friction restriction upon being inserted and retracted from the standard rack.

Standard racks offering friction restrictions over the entire well surface are also well-known in the art, such as e.g. standard racks made from polystyrene foam or injection molded plastics, both types of racks having small negative tolerances, with the small negative tolerance offering sufficient resistance to insertion and retraction of the test tube without blocking the movement of the test tube completely.

A problem in automated capping and de-capping of test tubes in standard racks is that currently existing standard racks are not all equally suitable for use in automated capping and de-capping. Particularly, it is a necessary requirement of the assembly of the test tube inside a standard rack that there is sufficient friction between test tube and standard rack to counteract the torsional forces exerted on the test tube by the automated capping and de-capping device during the capping and de-capping operations. For this reason, standard racks having negative tolerance well sizes are typically employed in automated capping and de-capping of test tubes, as they are particularly suited for providing the necessary friction force.

However, for various reasons, not all test tubes are suitable for use in automated capping and de-capping with a standard rack having a negative tolerance well size. E.g. tapered, in particularly conically tapered, test tubes are easily insertable and retractable from negative tolerance wells, in particularly since either the well or the test tube, or both, are usually designed to be slightly deformable under the pressure of insertion. Such test tubes therefore are well suited for automated capping- and de-capping. However, test tubes which are e.g. smooth, brittle, overly deformable (e.g. blow-molded test tubes), flat-bottomed etc. are currently difficult to automatically cap and de-cap in standard SBS test tube racks.

A current solution to some of the problems detailed above (cf. http://biosero.com/capping-decapping/vialcap24/—including a YouTube video clip, visited Jan. 26, 2015); combines a customized SBS format rack with an automated capping and de-capping device (VialCap24, Biosero) for use with flat bottomed glass vials comprising screw caps. The capping and de-capping operation displayed at the home page and in the video clip involves clamping of all screw caps in a cap holder and simultaneously rotation of the glass vials in the customized SBS format rack coupled with an upward (de-capping) or downward (capping) motion of the cap holder. Rotation of the glass vials is effected by a plurality of rotation wheels operating simultaneously. The rotation wheels exert a friction force on the glass which during operation (as can be seen from the video clip) is large enough to rotate the glass vials while also being large enough to hold the vials in the rack during the movement of the cap holder upwards during the de-capping operation. From the video clip it appears that the glass vials are pinched or clamped between at least two, but apparently between four rotation wheels during the de-capping operation displayed, thereby increasing the friction between the rotation wheels and the glass vials during the de-capping.

This customized SBS format rack can (according the homepage) be made from metal (aluminum) or plastics (PTFE) and is constructed as a two tier assembly with a top tier having a standard SBS format rack layout with circular holes for the glass vials and a bottom tier consisting of a net-like structure of open quadratic tiles having solid metal or plastic borders between tiles, and the tile surfaces being void of material to allow the aforementioned rotation wheels to protrude through the open tiles during operation of the de-capper and contact the vials on their rounded sides. The two tiers are attached on a frame structure whereby the tiers become spaced apart by a distance of about a third of the length of the glass vial and screw cap. The construction of the rack and use with the intended capping and de-capping apparatus makes this rack unsuited for uses where only individual capping and de-capping is intended.

The present invention concerns a SBS-standard test tube rack which is suitable for use in automated capping and de-capping of flat bottomed test tubes, in particular of flat bottomed glass vials, both for individual test tube capping and de-capping as well as simultaneous capping and de-capping of all test tubes in the aforementioned SBS-standard test tube rack, in particular being suitable for use with the automated capping and de-capping apparatus detailed in WO 2014023683.

SUMMARY OF THE INVENTION

The present invention relates in a first aspect and first embodiment to a SBS-standard test tube rack (20) for receiving a SBS-standard test tube rack compliant screw-capped test tube (10) of length (l) and diameter (d), said rack comprising: a top tier (22), support structure (23a,23b,23c, 23d) and a bottom tier (24), said support structure located between said top tier and said bottom tier, said top tier and bottom tier being, when assembled to form said rack (20), spaced apart a distance smaller than said length (l) by said support structure; said top tier (22) comprising a plurality of apertures (21) of aperture diameter (da) larger than said diameter (d), said apertures arranged to form a 2-dimensional array of apertures in said top tier; said bottom tier (24) comprising a friction tier (34) and a support tier (35); said friction tier facing said top tier (22) when said rack (20) is assembled; said friction tier (34) comprising a high friction material; wherein, when said rack (20) is assembled, there is formed an array of rack wells (30), each rack well (30) comprising an aperture (21), a well bottom (31) of well bottom diameter (dw) larger than said diameter (d), located opposite said aperture (21), and optionally a well enclosure (32) connecting said well bottom to said aperture either in a straight manner or conically tapering towards said well bottom (31), such that said aperture diameter (da) may be either slightly larger or of the same diameter as said well bottom diameter (dw); and wherein when said rack is assembled, said well bottom (31) is formed from said high friction material comprised in said friction tier (34).

In a second embodiment, the present invention relates to a SBS-standard test tube rack (20) of the first embodiment, wherein two or more of said top tier (22), said support structure (23a,23b,23c,23d), and support tier (35) can be of unitary construction In a third embodiment, the present invention relates to a SBS-standard test tube rack (20) of the first or second embodiment, wherein said aperture (21) is enlarged by a guiding section (33); which has a second and larger diameter than said aperture diameter (da).

In a fourth embodiment, the present invention relates to a SBS-standard test tube rack (20) of the first, second or third embodiment, wherein said well bottom (31) is recessed a small distance into said friction tier (34), thereby forming a small, independent well (41) in said friction tier.

In a fifth embodiment, the present invention relates to a SBS-standard test tube rack (20) according to any of the first to fourth embodiments, wherein said high friction material is selected from natural rubber, EPDM rubber, PVC-rubber, structured rubber or silicone, nonslip silicone, nonslip autoclavable silicone, sticky silicone, or is a compression-induce adhesive.

In a sixth embodiment, the present invention relates to a SBS-standard test tube rack (20) according to any of the first to fifth embodiments, wherein said test tube (10) is a standard laboratory 15 mm Ø×45 mm flat bottom glass vial (10) mounted with a screw cap (14).

In a seventh embodiment, the present invention relates to a method of capping or de-capping a SBS-standard test tube rack compliant screw-capped test tube (10) supported upright in a rack well (30) comprising a well bottom (31) in a SBS-standard test tube rack (20) according to any of the above embodiments, said rack (20) positioned in an apparatus for automated test tube capping and de-capping opposite in the upright direction a capping and de-capping gripper comprised in said apparatus, said method comprising engaging said gripper to said test tube (10) and exerting a downwards force by said gripper on said test tube (10) to create a frictional force between said test tube (10) and said well bottom (31) of said rack (20) which exceeds a torsional force sufficient to cap or de-cap said test tube (10) by rotation of said gripper in a direction suitable for capping or de-capping said test tube (10), without said test tube (10) co-rotating with said gripper in the direction of said gripper's rotation.

DETAILED DESCRIPTION

Figure 1:
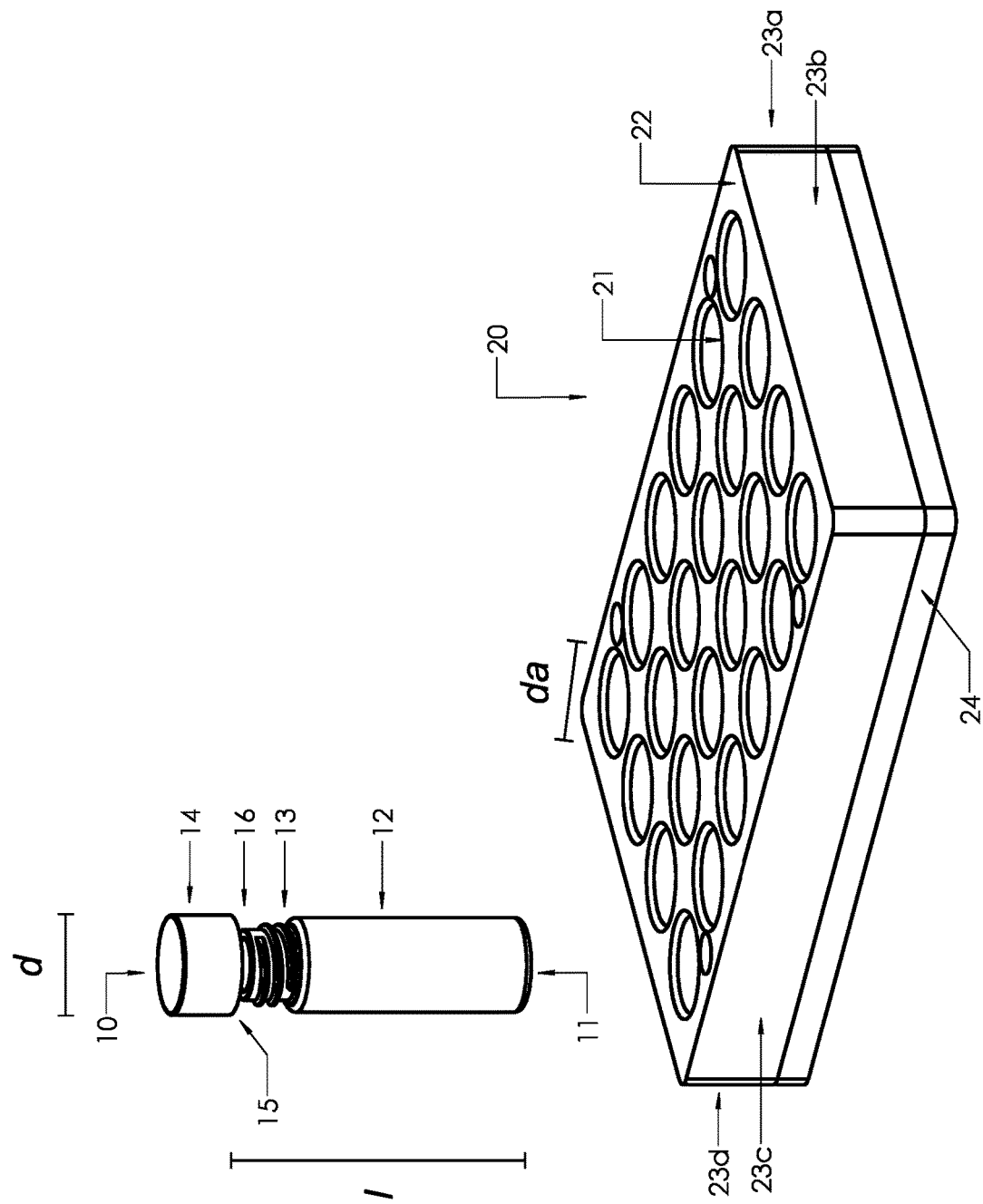
FIG. 1: A flat bottomed test tube (A) and a SBS-standard test tube rack (B).

FIG. 1 (A) details a SBS-standard test tube rack (20) compliant test tube (10) of a certain length (l) and cross-sectional diameter (d) and with a screw cap (14), the screw cap as shown comprising an internal thread (15). The test tube comprises an opening (16), a cylindrical envelope (12), an external thread (13) on the cylindrical envelope, complementary to the internal thread of the screw cap, to allow the screw cap to releasably attach and detach from the test tube, and a substantially flat test tube bottom (11), located opposite the test tube opening with the cylindrical envelope spaced between the opening and the bottom. The test tube when closed defines an inner surface for contacting test samples and an outer surface in contact with the surroundings, and the surfaces of the cylindrical envelope (12) and test tube bottom (11) can be defined as inner or outer surfaces in the same manner.

FIG. 1 (B) details a SBS-standard test tube rack (20) with a plurality of apertures (21) of diameter (da) located on a top tier (22) and adapted to permit the passage of a test tube (10) of length (l) and having a cross-sectional diameter (d) or smaller through said apertures. The apertures of the plurality of apertures are placed to form a 2-dimensional array of apertures. The rack further comprises a support structure (23a,23b,23c,23d) e.g. in the form of four sides (23a,23b, 23c,23d) and a bottom tier (24). Optionally, the four sides can be substituted for a plurality of upright posts, serving the same function of structurally stabilizing the rack and keeping the top and bottom tiers spaced apart at a distance, which is smaller than the length (l) of the test tube. Depending on their intended uses, SBS racks may be constructed as closed structures comprising a plurality of rack wells (30) wherein a test tube (10) can be received and at least partially contained or as two tier constructions, wherein the upper tier stops the test tubes from tumbling over during transport and use, and the bottom tier hinders that test tubes inserted through the apertures of the top tier can pass through the apertures over the entire length of the test tube. In a particular embodiment of the closed structure rack, top tier (22) and support structure (23a,23b,23c,23d) are combined by manufacturing the top tier (22) as a solid block of the desired thickness with throughbores serving as rack wells for the SBS-standard rack.

Figure 2:
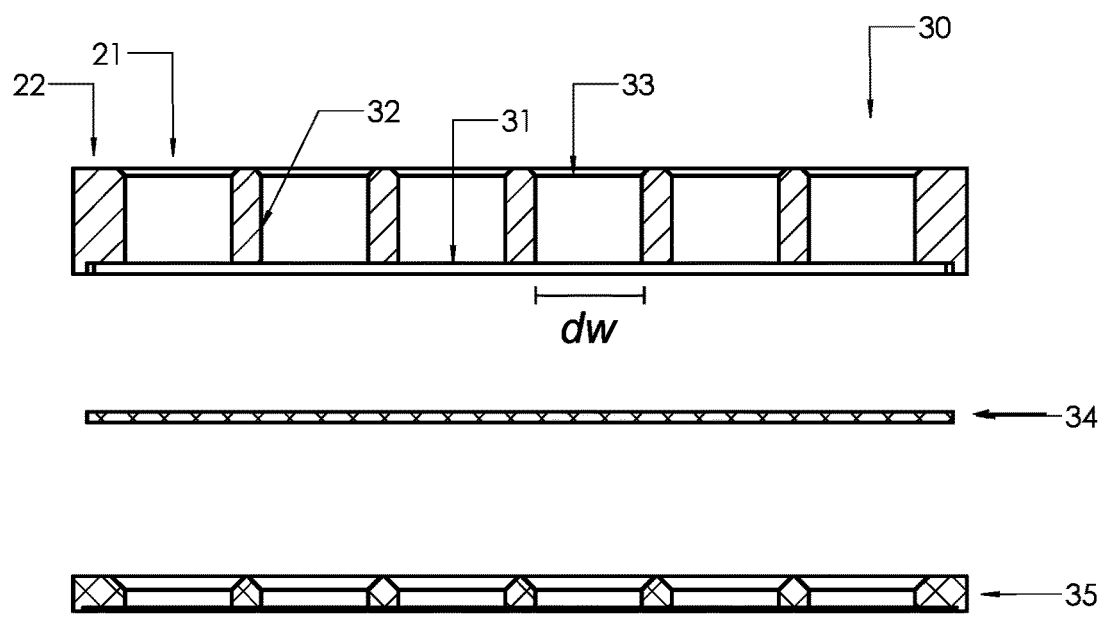
FIG. 2: A rack well in the SBS-standard test tube rack according to the invention.

FIG. 2 shows a cross-section of a rack well (30) according to the invention.

A rack well (30) for a SBS-standard test tube rack (20) according to the present invention comprises the aforementioned aperture (21) comprised in said top tier (22); a well bottom (31); optionally a well enclosure (32), which may be connected in a straight manner or be conically tapering towards the well bottom (31), the well bottom located opposite the aforementioned aperture (21), such that the aperture diameter may be either slightly larger or of the same diameter as the well bottom diameter.

In the figure, the diameter (dw) of the well bottom is determined by the diameter (d) of the test tube bottom (11) at its largest cross-section such that when a test tube (10) is inserted into the rack well (30) through the aperture (21), the test tube bottom (11) can be in contact with the well bottom (31) over its entire outer surface. A slight positive tolerance of maximum 5% is preferable for the well bottom diameter compared to the test tube bottom but, as will be explained below, in some cases the tolerance at the well bottom may be 0% or even negative.

In the figure, the aperture (21) diameter (da) is either larger than or equal to the well bottom (31) diameter; the well enclosure (32) will guide the test tube (10) towards the well bottom (31). It promotes an easier insertion of test tubes into the apertures of the rack, when the aperture (21) is larger in diameter that the well bottom. However, in order to keep the test tubes (10) from tumbling around when inserted into the rack wells (30) of the rack (20), the aperture diameter cannot be much larger than the well bottom diameter. Aperture diameters up to about 10% larger than well bottom diameters have proven reasonable. Some test tubes suitable for use with a SBS-standard test tube rack are conically shaped or rounded or do not have a substantially uniform cross-section, characterizable by a single cross-sectional diameter. In such cases, the skilled person will know how to adapt the wells to permit entry of the test tube into these wells, while retaining the guiding and stabilizing functions of the wells described above.

Preferred, however, an aperture (21) in some embodiments of the rack well (30) can be enlarged by a guiding section (33) which has a second and larger diameter than the aperture diameter, wherein the guiding section is intended for guiding a test tube (10) outside the aforementioned rack well and into the rack well (30). This is particularly advantageous in automated test tube rack filling operations, as it lowers the requirements on the steering accuracy of the test tube rack filling devices.

A high friction material forms a friction tier (34) which is used for forming the well bottom (31) when the rack is assembled. A high friction material in the sense of the present disclosure is, in general, a material that is recognized as having has a high static or kinetic friction coefficient with other materials, such as e.g. natural rubber or artificial rubber, e.g. EPDM or PVC-rubber or silicone rubber (e.g. nonslip friction mat). Alternatively, the well bottom may comprise a material which is slightly tacky or is a compression induced adhesive (e.g. a compression sensitive polyacrylate, e.g. clean room tacky mat). It is further advantageous that the friction tier (34) rests on a support tier (35) for mechanical support, the support tier manufactured from a metal or a hard plastics material. Together, friction tier (34) and support tier (35) form the aforementioned bottom tier (24).

It is within the skills of the artisan to determine what constitutes a suitable high friction material following the laws of classical mechanics. The torque necessary to cap and de-cap a screw-cap test tube can easily be measured (e.g. by using the apparatus of WO 2014023683) and therethrough the torsional force, which must be counteracted by the friction force between test tube (10) and friction tier (34) for the test tube to remain stationary during the capping and de-capping operations. As the force with which the test tube acts on the friction tier is largely given by the downwards pressure exerted by the capping and de-capping apparatus during the capping and de-capping operations (with a slight gravitational contribution from the test tube) a suitable high friction material for the friction tier is a material with a sufficient static friction coefficient to the test tube material such that the product of static friction coefficient and downwards force acting on the friction tier becomes larger than the torsional forces acting on the test tube during the capping and de-capping operations.

In an embodiment of the bottom tier (24), the friction tier (34) and support tier (35) are manufactured from one material, e.g. rubber or from plastics. In some embodiments increased friction has been created by structuring that surface of the bottom tier, which will contact the test tube (10), whereby the structured surface becomes the friction tier (34) and the non-structured part of the bottom tier (24) becomes the support tier (35).

Figure 3:
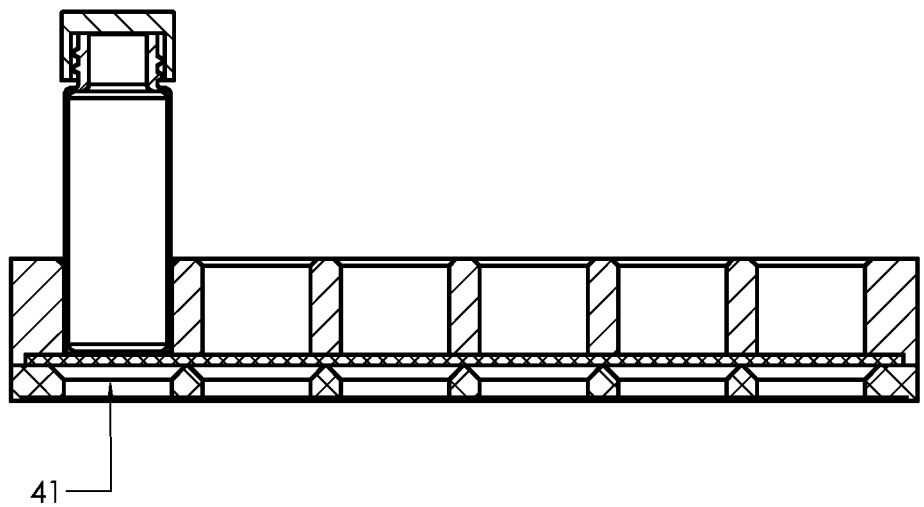
FIG. 3: A well bottom in the SBS-standard test tube rack according to the invention.
Figure 4:
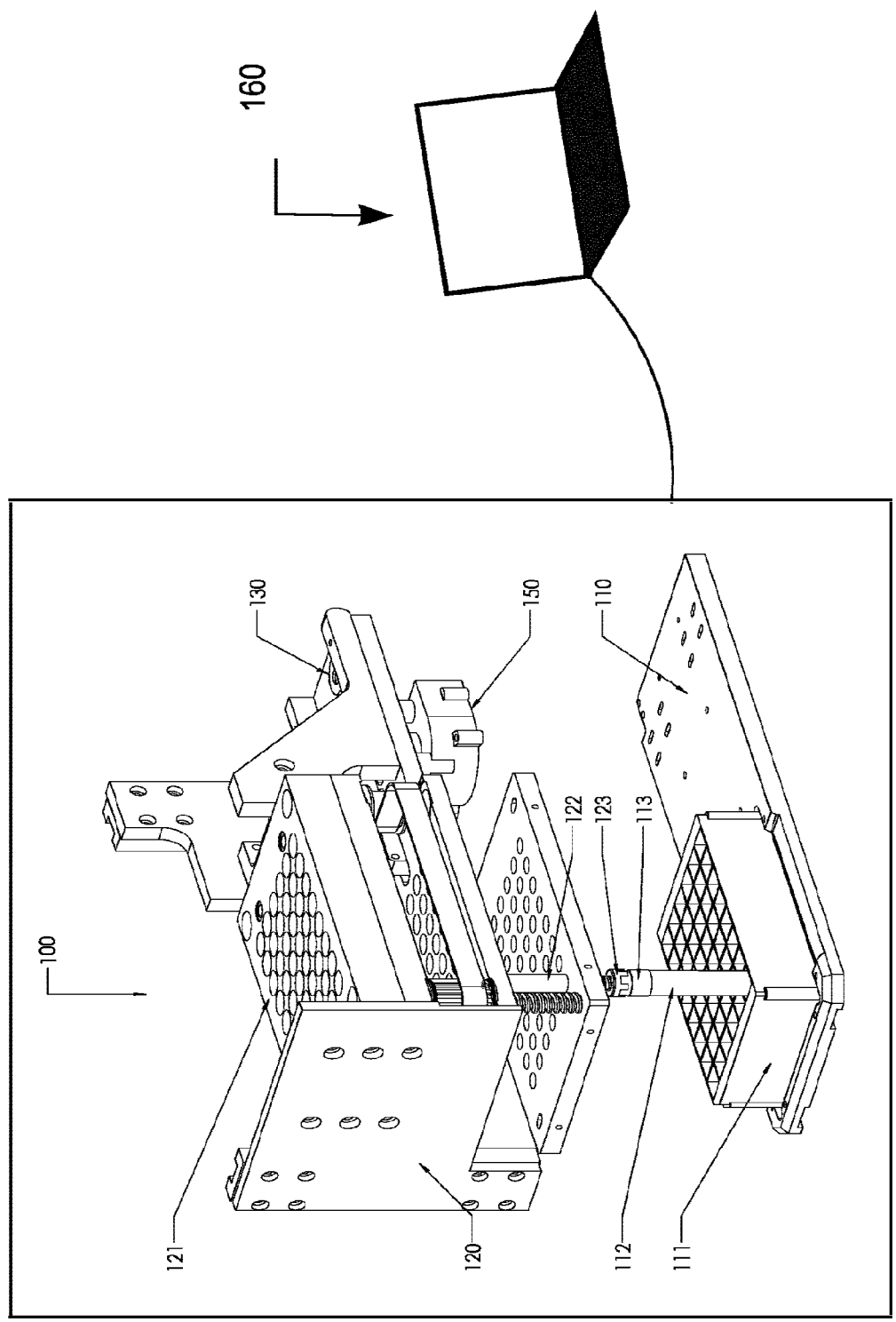
FIG. 4: An automated capping and de-capping apparatus suitable for use in a method of capping and de-capping a test tube rack according to an embodiment of the invention.

In an embodiment (FIG. 3), the well bottom (31) is recessed a small distance into the friction tier (34), forming a small, independent well (41) in the friction tier. When the friction tier is manufactured from a compressible material, such as e.g. rubber or an adhesive, the small, independent well (41) can in fact have a slightly negative tolerance diameter compared to the diameter of the test tube bottom (11). As the automated capping and de-capping device as mentioned already normally exerts a small pressure on the screw cap and test tube assembly, this aids in securing an improved contact between test tube and well bottom, and thereby an increased friction force to counter the torsional forces exerted on the test tube during capping and de-capping. A friction tier (34) comprising one or more of such small, independent wells (41), can easily be manufactured by the skilled person, e.g. by injection molding of rubber or silicone.

In the embodiments of the invention described above, the friction tier (34) has been illustrated as a sheet in the figures. However, well bottoms (31) comprising a high friction material can be manufactured in other ways as will be apparent to the skilled person based on the below description. For example, the friction tier could be manufactured as inserts glued into individual wells, sprayed into individual wells, co-molded into the wells, or insert molded into the wells. In some embodiments, two or more of the top tier and the support layer, and support tier 35 are one piece and the friction material is added to the well bottoms after formation or can be co-molded or insert molded. A friction tier (34) could also be insert molded, co-molded, sprayed on, or be individual pads glued onto the support tier (35).

In the above figures, the function of the test tube rack of the invention has been described with reference to standard 15 mm Ø×45 mm flat bottom test vials comprising a threading arrangement, wherein the screw-caps are internally threaded and the vials externally threaded. The skilled person will realize, e.g. based on the disclosure of WO 2014023683, that any threading arrangement of the test tubes for use with the racks of the invention is suitable for use, including a cap with an external thread for a tube with internal threading. Neither is the invention limited to flat bottom test vials only, rather any SBS-standard compliant test tube can be used including such with convex bottoms or with bottoms that are symmetric with respect to a longitudinal axis of the tube.

However, preferred test tubes (10) for use with present invention are standard 15 mm Ø×45 mm flat bottom test vials, preferably made from glass or plastics like POM or PEEK, most preferably made from glass. However, the test tube may also be made from softer plastics, e.g. PE or PS which will deform if too much downwards pressure is exerted on the test tube during the capping and de-capping operations. In the latter cases, particular attention to finding a proper match between high friction material and test tube is required. In such cases, non-slip silicone or tacky friction materials are preferred.

Further, in an embodiment, the present invention relates to a method of capping or de-capping a SBS-standard test tube rack compliant screw-capped test tube (10) supported upright in a rack well (30) comprising a well bottom (31) in a SBS-standard test tube rack (20) according to any of the above embodiments, wherein upright and downwards are describe relative to Earth's gravitational field according to their normal use in daily language. The rack (20) is then positioned in an apparatus (e.g. the apparatus of WO 2014023683) for automated test tube capping and de-capping opposite in the upright direction a capping and de-capping gripper comprised in the apparatus, the method comprising engaging the gripper to the test tube (10) and exerting a downwards force by the gripper on the test tube (10) to create a frictional force between the test tube (10) and the well bottom (31) of the rack (20) which exceeds a torsional force sufficient to cap or de-cap the test tube (10) by rotation of the gripper in a direction suitable for capping or de-capping the test tube (10) without the test tube (10) co-rotating with the gripper in the direction of the gripper's rotation.

EXAMPLES

A model SBS-standard test tube rack was constructed comprising a top tier wherein rack wells were drilled in a 30 mm block of aluminum of appropriate dimensions for an SBS rack, to form an array of apertures conferring to a standard size SBS test tube rack for 15 mm Ø×45 mm flat bottom glass vials (4×6 glass vials per rack). The wells were drilled through the top tier without inclination and at 7% positive tolerance (16 mm Ø) to allow unhindered insertion of the test tubes. A support tier was manufactured in 2 mm aluminum. The top tier and support tier were provided with threaded holes in each corner and assembled to form the model SBS size rack using screws with a well bottom of aluminum. The top tier and bottom tier were spaced apart by 15 mm.

A test using standard laboratory 15 mm Ø×45 mm flat bottom glass vials mounted with screw caps, the capping and de-capping apparatus of WO 2014023683 and the model SBS-rack described above, failed to de-cap the vials; as glass vials and mounted screw caps would co-rotate in spite of the slight additional pressure exerted by the de-capper on the vial and screw cap assembly.

In a next step, friction tiers were manufactured from various nonslip materials commercially available as folios of 1-2 mm thickness. The friction tiers were inserted between the top tier and the support tier, thereby creating an SBS test tube rack of the invention, and changing the well bottom material from aluminum to a nonslip material to be tested.

Tests comprised using 1 mm natural rubber folio, 1 mm EPDM rubber folio, structured 1 mm EPDM rubber folio, 2 mm nonslip silicone folio autoclavable, 1 mm sticky silicone folio (cell phone cover), and 2 mm sticky entrance mat for clean rooms consisting of a low density polyethylene carrier layer with an acrylic-rubber easy slip adhesive. All six test materials were found to provide adequate friction for the glass vials during the capping and de-capping operations.

The autoclavable nonslip silicone folio was further tested for use after having been autoclaved and was found to retain its nonslip properties and suitability for use in the rack of the invention and during automated capping and de-capping operations. The ability to autoclave a rack of the present invention is, naturally, in a laboratory environment where biological samples are handled in glass vials, very important.

CLOSING COMMENTS

The term "comprising" as used in the claims does not exclude other elements or steps. The term "a" or "an" as used in the claims does not exclude a plurality. A single processor or other unit may fulfill the functions of several means recited in the claims. Although the present invention has been described in detail for purpose of illustration, it is understood that such detail is solely for that purpose, and variations can be made therein by those skilled in the art without departing from the scope of the invention.

The invention claimed is:

1. A test tube rack for receiving a test tube rack compliant screw-capped test tube of length (l) and diameter (d), said rack comprising:
    a top tier and a bottom tier, a top surface of said top tier and said bottom tier being, when the top tier and bottom tier are assembled to form said rack, spaced apart a distance smaller than said length (l);
    said top tier comprising a plurality of apertures of aperture diameter (da) larger than said diameter (d), said apertures arranged to form a 2-dimensional array of apertures in said top tier;
    said bottom tier comprising a friction tier and a support tier having independent wells, the friction tier comprising a sheet of high friction material closing the independent wells;
    said friction tier facing said top tier when said rack is assembled;
    wherein, when said rack is assembled, there is formed an array of rack wells, each rack well comprising an aperture of the plurality of apertures and a well bottom of well bottom diameter (dw) larger than said diameter (d), located opposite said aperture; and
    wherein when said rack is assembled, said well bottom is formed from said high friction material comprised in said friction tier.

2. A test tube rack of claim 1, wherein the top tier includes a support structure, and wherein two or more elements chosen from the list of said top tier, said support structure, and said support tier are of unitary construction.

3. A test tube rack according to claim 1, wherein said aperture of each rack well is enlarged by a guiding section; which has a second and larger diameter than said aperture diameter (da).

4. A test tube rack according to claim 1, wherein said high friction material is selected from natural rubber, EPDM rubber, PVC-rubber, structured natural or silicone, nonslip silicone, nonslip autoclavable silicone, sticky silicone, or is a compression-induce adhesive.

5. A test tube rack according to claim 1, wherein each rack well is configured to receive a test tube that is a 15 mm Ø×45 mm flat bottom glass vial mounted with a screw cap.

6. A test tube rack according to claim 1, further comprising a well enclosure connecting said well bottom to said aperture, such that said aperture diameter (da) is either slightly larger or of the same diameter as said well bottom diameter (dw).

7. A method of capping or de-capping a test tube rack compliant screw-capped test tube supported upright in a rack well comprising a well bottom in a test tube rack, the test tube rack comprising
    a top tier and a bottom tier, a top surface of said top tier and said bottom tier being, when the top tier and bottom tier are assembled to form said rack, spaced apart a distance smaller than said length (l),
    said top tier comprising a plurality of apertures of aperture diameter (da) larger than said diameter (d), said apertures arranged to form a 2-dimensional array of apertures in said top tier;
    said bottom tier comprising a friction tier and a support tier;
    said friction tier facing said top tier when said rack is assembled;
    said friction tier comprising a high friction material;
    wherein, when said rack is assembled, there is formed an array of rack wells, each rack well comprising an aperture of the plurality of apertures and a well bottom of well bottom diameter (dw) larger than said diameter (d), located opposite said aperture; and
    wherein when said rack is assembled, said well bottom is formed from said high friction material comprised in said friction tier;
    said rack positioned in an apparatus for automated test tube capping and de-capping opposite a capping and de-capping gripper comprised in said apparatus, said method comprising:
    engaging said gripper to said test tube and exerting a downwards force by said gripper on said test tube to create a frictional force between said test tube and said well bottom of said rack which exceeds a torsional force to cap or de-cap said test tube by rotation of said gripper in a direction for capping or de-capping said test tube, without said test tube co-rotating with said gripper in the direction of said gripper's rotation.

8. A test tube rack in combination with screw-capped test tubes, comprising:
    test tube rack compliant screw-capped test tubes, each of length (l) and diameter (d); and
    a test tube rack for receiving the test tube, the rack comprising
    a top tier and a bottom tier, a top surface of said top tier and said bottom tier being, when the top tier and bottom tier are assembled to form said rack, spaced apart a distance smaller than said length (l);
    said top tier comprising a plurality of apertures of aperture diameter (da) larger than said diameter (d), said apertures arranged to form a 2-dimensional array of apertures in said top tier;
    said bottom tier comprising a friction tier and a support tier;
    said friction tier facing said top tier when said rack is assembled;
    said friction tier comprising a high friction material;
    wherein, when said rack is assembled, there is formed an array of rack wells, each rack well comprising an aperture of the plurality of apertures and a well bottom of well bottom diameter (dw) larger than said diameter (d), located opposite said aperture;
    wherein when said rack is assembled, said well bottom is formed from said high friction material comprised in said friction tier; and
    wherein the screw-capped test tubes are positioned in the rack wells with bottom ends resting against the high friction material.

* * * * *